(12) United States Patent
Clime et al.

(10) Patent No.: US 9,442,108 B2
(45) Date of Patent: Sep. 13, 2016

(54) CENTRIFUGALLY-ENHANCED CAPTURE METHOD AND DEVICE

(75) Inventors: Liviu Clime, Longueuil (CA); Xuyen Dai Hoa, Montreal (CA); Teodor Veres, Montreal (CA); Francois Normandin, Montreal (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

(21) Appl. No.: 14/342,198

(22) PCT Filed: Aug. 27, 2012

(86) PCT No.: PCT/CA2012/000794
§ 371 (c)(1),
(2), (4) Date: Feb. 28, 2014

(87) PCT Pub. No.: WO2013/029153
PCT Pub. Date: Mar. 7, 2013

(65) Prior Publication Data
US 2014/0212992 A1    Jul. 31, 2014

Related U.S. Application Data

(60) Provisional application No. 61/528,883, filed on Aug. 30, 2011.

(51) Int. Cl.
*B01L 3/00* (2006.01)
*G01N 33/543* (2006.01)

(52) U.S. Cl.
CPC ..... *G01N 33/54306* (2013.01); *B01L 3/50273* (2013.01); *B01L 3/502761* (2013.01);
(Continued)

(58) Field of Classification Search
CPC .......... G01N 2035/00574; G01N 2021/1721; G01N 2021/1727; G01N 21/1717; G01N 21/552; G01N 21/648; G01N 2201/0691; G01N 23/04; G01N 2015/149; G01N 2021/6417; G01N 2035/00782; G01N 21/645; G01N 21/88; G01N 21/951; G01N 21/952; G01N 2223/419; G01N 23/046; G01N 35/10; B01L 2200/0657; B01L 2400/049; B01L 3/021
USPC ............... 422/69; 435/283.1, 287.2; 436/501
See application file for complete search history.

(56) References Cited

U.S. PATENT DOCUMENTS 5,961,846 A * 10/1999 Borchardt ............. B04B 5/0442
                                                          210/781
6,818,435 B2    11/2004 Carvalho et al.
(Continued)

FOREIGN PATENT DOCUMENTS

WO    WO2010077159    7/2010

OTHER PUBLICATIONS

Amaglianig, et al. (2004) Direct detection of Listeria monocytogenes from milk by magnetic based DNA isolation and PCR. Food Microbiology. 21(5), 597-603.
(Continued)

*Primary Examiner* — Erik B Crawford
(74) *Attorney, Agent, or Firm* — Jason E. J. Davis

(57) ABSTRACT

In a centrifugal microfluidic device for conducting capture assays, a microfluidic platform rotates in a plane of rotation and has at least one capture surface for immobilizing a target particle of interest in the device. The capture surface oriented so that it is not parallel to the plane of rotation of the device and is positionally fixed in the device during operation of the device. The centrifugal force arising from rotation of the device forces the target particles against the capture surface. Capture efficiency is independent of the rate of flow of the fluid and independent of the rate of rotation of the microfluidic platform.

19 Claims, 2 Drawing Sheets

(52) U.S. Cl.
CPC . *G01N33/54366* (2013.01); *B01L 2300/0636* (2013.01); *B01L 2300/0803* (2013.01); *B01L 2300/0858* (2013.01); *B01L 2400/0409* (2013.01)

(56) References Cited

U.S. PATENT DOCUMENTS

| | | | |
|---|---|---|---|
| 7,026,131 | B2 | 4/2006 | Hurt et al. |
| 7,041,258 | B2 | 5/2006 | Desmond et al. |
| 7,150,812 | B2 | 12/2006 | Huang et al. |
| 7,152,616 | B2 | 12/2006 | Zucchelli et al. |
| 7,157,049 | B2 | 1/2007 | Valencia et al. |
| 7,295,320 | B2 | 11/2007 | Ostlin et al. |
| 7,332,126 | B2 | 2/2008 | Tooke et al. |
| 7,692,794 | B2 | 4/2010 | Kim et al. |
| 7,776,267 | B2 | 8/2010 | Lee et al. |
| 2002/0001803 | A1 | 1/2002 | Smith |
| 2003/0053934 | A1 | 3/2003 | Andersson et al. |
| 2005/0047968 | A1 | 3/2005 | Kido et al. |
| 2005/0170354 | A1* | 8/2005 | Munch-Fals ............ 435/6 |
| 2007/0026419 | A1 | 2/2007 | Fuchs |
| 2007/0224591 | A1 | 9/2007 | Gui et al. |
| 2008/0138247 | A1 | 6/2008 | Inganas et al. |
| 2008/0241000 | A1 | 10/2008 | Jung et al. |
| 2009/0029353 | A1* | 1/2009 | Maki et al. ............ 435/6 |
| 2010/0041562 | A1 | 2/2010 | Li et al. |
| 2010/0055766 | A1 | 3/2010 | Hwang |
| 2010/0081213 | A1 | 4/2010 | Lee |
| 2011/0003285 | A1 | 1/2011 | Niwa |
| 2011/0020194 | A1 | 1/2011 | Lee et al. |

OTHER PUBLICATIONS

Choi J-W, et al. (2006) Bacteria Detection in a Microfluidic Channel Utilizing Electromagnetic Cellular Polarization and Optical Scattering. 2006 Digest of the LEOS Summer Topical Meetings. 2, 17-18.
Choi W. (2002) Rapid enumeration of Listeria monocytogenes in milk using competitive PCR. International journal of food microbiology. 84, 79-85.
Dwivedi HP, Jaykus LA. (2011) Detection of pathogens in foods: The current state-of-the-art and future directions. Critical Reviews in Microbiology. 37(1), 40-63.
Firstenberg-Eden R, Shelef LA. (2000) A new rapid automated method for the detection of Listeria from environmental swabs and sponges. International journal of food microbiology. 56(2-3), 231-237.
Garcia-Cordero, JL, et al. (2009) Monolithic Centrifugal Microfluidic Platform for Bacteria Capture and Concentration, Lysis, Nucleic-Acid Amplification, and Real-Time Detection. MEMS 2009—22nd IEEE International Conference on Micro Electro Mechanical Systems. pp. 356-359.
Ingianni A, et al. (2001) Rapid detection of Listeria monocytogenes in foods, by a combination of PCR and DNA probe. Molecular and cellular probes. 15(5), 275-280.
Kaittanis C, et al. (2007) One-Step, Nanoparticle-Mediated Bacterial Detection with Magnetic Relaxation. Nano Letters. 7(2), 380-383.
Koubova V, et al. (2001) Detection of foodborne pathogens using surface plasmon resonance biosensors. Sensors and Actuators B: Chemical. 74(1-3), 100-105.
Li H, et al (2002) Dielectrophoretic separation and manipulation of live and heat-treated cells of Listeria on microfabricated devices with interdigitated electrodes. Sensors and Actuators B: Chemical. 86(2-3), 215-221.
Madonna AJ, et al. (2001) Detection of bacteria from biological mixtures using immunomagnetic separation combined with matrix-assisted laser desorption/ionization time-of-flight mass spectrometry. Rapid communications in mass spectrometry : RCM. 15(13), 1068-1074.
Nolte DD. (2009) Review of centrifugal microfluidic and bio-optical disks. Review of Scientific Instruments. 80, 101101 (22 pages).
Sewell AM, et al. (2003) The development of an efficient and rapid enzyme linked fluorescent assay method for the detection of *Listeria* spp. from foods. International journal of food microbiology. 81(2), 123-129.
Su X-L, (2004) Quantum dot biolabeling coupled with immunomagnetic separation for detection of *Escherichia coli* O157:H7. Analytical chemistry. 76(16), 4806-4810.
Vaughan R, et al. (2001) Development of a quartz crystal microbalance (QCM) immunosensor for the detection of Listeria monocytogenes. Enzyme and microbial technology. 29(10), 635-638.
Wawerla M et al. (1999) Impedance Microbiology: Applications in Food Hygiene. Journal of Food Protection. 62, 1488-1496.
Yang L, et al. (2006) A multifunctional micro-fluidic system for dielectrophoretic concentration coupled with immuno-capture of low numbers of Listeria monocytogenes. Lab on a chip. 6(7), 896-905.
Zeng L. et al. (2005) Wall-induced forces on a rigid sphere at finite Reynolds number. Journal of Fluid Mechanics. 536, 1-25.
International Search Report for corresponding PCT/CA2012/000794 mailed on Dec. 27, 2012.
International Report on Patentability and Written Opinion for corresponding PCT/CA2012/000794 mailed on Mar. 4, 2014.
Extended European Search Report for corresponding EP Application No. 12827166 mailed on Apr. 21, 2015.
Supplementary European Search Report for corresponding EP 12 82 7166 mailed on Apr. 21, 2015.

\* cited by examiner

CENTRIFUGALLY-ENHANCED CAPTURE METHOD AND DEVICE

CROSS-REFERENCE TO RELATED APPLICATIONS

This application is a national phase entry of International Patent Application No. PCT/CA2012/000794 filed Aug. 27, 2012 and claims the benefit of U.S. Provisional Patent Application Ser. No. USSN 61/528,883 filed Aug. 30, 2011, the entire contents of both of which are herein incorporated by reference.

FIELD OF THE INVENTION

The present invention relates to methods and devices for capturing and detecting target molecule in a sample. In particular, the present invention related to microfluidic devices having centrifugally enhanced capture capability.

BACKGROUND OF THE INVENTION

The capture and isolation of biological targets (pathogens, bacteria, cells, functionalized micro-beads, etc.) are critically important in many clinical diagnostic, screening, environmental assessment and quality control applications. For many of these applications, there is a need for rapid and low-cost detection/identification assays. In the area of food safety, foodborne disease is a serious public health threat and thus rapid detection of potentially life-threatening pathogens remains a major public health challenge (Yang 2006). Similar challenges are found in the field of clinical diagnostics where rapid detection of pathogens in a patient's blood is sought; and in environmental and biosecurity applications where identification of bacteria and other contaminants from water samples are desired. Over the past several years, a variety of methods have been investigated for the detection of bacteria and other biological targets in food or water, for example, immunological assays (Koubová 2001; Vaughan 2001; Sewell 2003), nucleic acid-based tests (Ingianni 2001; Choi 2002; Amagliani 2004) and physicochemical tests based on bacterial growth (Wawerla 1999; Firstenberg-Eden 2000).

Among the above mentioned methods, immuno-capture based assays are of great interest due to the high sensitivity and specificity of antigen-antibody immuno-interaction. Antigens present on surfaces of species/objects of interest (pathogens, bacteria, microbeads) suspended in a biological fluid/sample are captured by specific antibodies immobilized on to a surface. While the antigen-antibody interaction have been primarily used in the immuno-capture assays, various techniques can replace this interaction with other moieties such as aptamers (peptides/oligonucleotide sequences) and biophages that are thought be provide better capture (Zourob 2008). In such assays, the probability of capture of the targets is directly related to the velocity of the fluid above the functionalized surface (antibody, biophage, aptamer-coated surface), with higher probability of capture being obtained at lower flow rates. The order of magnitude of the liquid velocity at which reasonable values for probability of capture are obtained ranges in the tens of micrometers per second. At these relatively slow flow rates and with the typical sample volumes in use in many biological protocols (milliliter to hundreds of microliters), an assay or analysis can take significant time, thus preventing rapid detection.

The main reason these extremely low flow rates are used in immuno and other capture assays originates in the hydrodynamic interaction of species or objects with the functionalized surface. Particles flowing near a rigid surface undergo a "wall effect" where an asymmetric wake of the particles near the surface leads to lift forces away from the surface (Zeng 2005). Thus, the "natural" tendency of functionalized rigid surfaces is to repel particles flowing near the surface, the repelling force being higher at higher velocities of the particles. Consequently, the velocity of the liquid must be as small as possible in order to allow particles to attach to the functionalized surfaces. The forces that naturally push the particles against the capture area of the surface are thermal, gravitational and diffusive effects in the biological liquid sample.

In order to increase the efficiency of species binding to functionalized capture sites, several methods have been proposed. One of them employs an array of interdigitated metallic electrodes and the dielectrophoretic force to give pathogens an additional push against the capture sites (Li 2002; Yang 2006). The dielectrophoretic force acting on pathogens originates in the ability of the pathogens to polarize in the presence of electric fields. This force can be adjusted by tuning the amplitude and frequency of the applied AC fields. An equivalent method employs electromagnetic cellular polarization and optical scattering for direct detection but without the use of any biochemical marker (Choi 2006).

One and the most important drawback of dielectrophoresis-based capture approaches is related to the short range action of the dielectrophoretic force itself, which, in practical microfluidic applications is only on the order of tenths of micrometers (Li 2002). This limits the size of the microfluidic channels, thus the overall throughput of the device. Moreover, the use of complicated arrays of electrodes increases the number of fabrication steps (thus the cost per unit device) associated with the electronics needed to generate the necessary high frequency AC voltages. This is detrimental when single-use, low-cost and portable devices for point-of-care applications are intended.

Another approach is based on immuno-magnetic capture and separation (Dwivedi 2011). Instead of forcing particles to bind to rigid (fixed) walls, the antibodies are deposited onto the surface of superparamagnetic beads. These beads become magnetic only in the presence of external magnetic fields and return immediately to the non-magnetized state as the magnetic field is removed. This is an important property for immuno-magnetic capture since the beads will freely interact with the target antigens (pathogens) in stagnant liquid suspensions without clustering together by mutual magnetic interactions. The process of capture can be slightly accelerated if moderate vortexing (agitation) of liquid suspensions is induced. Commercial devices, such as the well known BeadRetriever™ from Dynal Biotech Ltd. (Wirral, UK) based on the inverse magnetic particle processing principle, are able to reduce the capture time further by moving the particles along small tubes containing the sample with the aid of a magnetic bar. Related methods further decrease the detection time by adding features such as quantum dots for enhanced fluorescence (Su 2004), magnetic relaxation (Kaittanis 2007) and time-of-flight mass spectrometry (Madonna 2001).

In immuno-magnetic capture using superparamagnetic beads, the time needed by functionalized beads to bind to specific pathogens present in the sample may be lowered by stirring the solution to increase the probability of capture. However, the stirring speed is limited to the same fluid-tosolid relative velocities as in the static case, mainly due to the same hydrodynamic wall effect that manifests at the surface of moving beads. Consequently, the fundamental problem related to the wall effects that repel particles from functionalized surfaces is not addressed.

Immuno-magnetic capture using superparamagnetic beads may be implemented in microfluidic devices (e.g. Lee 2010; Lee 2011). The beads are used as a carrier surface for the capture of a target molecule. In these cases, centrifugal force generated by the rotating device is used to pump fluids through the device and to move the beads from chamber to chamber. Centrifugal force is not used to directionally immobilize target particles on to an immobile capture surface.

There remains a need for increasing capture efficiency of a target molecule in a capture assay in a microfluidic device.

SUMMARY OF THE INVENTION

In one aspect of the present invention there is provided a centrifugal microfluidic device for conducting capture assays, the device comprising a rotating microfluidic platform that rotates in a plane of rotation, the platform having at least one capture surface for immobilizing a target particle of interest in the device, the capture surface oriented so that it is not parallel to the plane of rotation of the device, the capture surface positionally fixed in the device during operation of the device, and centrifugal force arising from rotation of the device forces the target particles against the capture surface.

A method of capturing a target particle of interest for an assay in a centrifugal microfluidic device, the method comprising: introducing a fluid containing the target particle into a rotatable microfluidic platform of the microfluidic device; rotating the microfluidic platform in a plane of rotation to generate centrifugal force in the device; and, using the centrifugal force to direct flow of the fluid to a capture surface in the device thereby pushing the target particle against the capture surface to increase probability of the target particle interacting with the capture surface, wherein capture efficiency of the capture surface for the target particle is independent of rate of flow of the fluid and independent of rate of rotation of the microfluidic platform.

In existing centrifugal microfluidic devices centrifugal force generated by rotation of the platform is used exclusively to pump liquids from one place to another. Capture surfaces in the device are located on the bottom surface of the device parallel to the plane of rotation and parallel to the centrifugal force in the device. Target particles flow over the top of the capture surface but target particle/capture site interactions depend on thermal, gravitational and diffusive effects to occur. As previously stated, particles flowing near a rigid surface undergo a "wall effect" where an asymmetric wake of the particles near the surface leads to lift forces away from the surface. Thus, the "natural" tendency of rigid surfaces is to repel particles flowing near the surface, the repelling force being higher at higher velocities of the particles. Consequently, the velocity of the liquid must be as small as possible in order to allow particles to attach to the capture surface. Since the forces that naturally push the particles against the capture surface are thermal, gravitational and diffusive effects, existing centrifugal microfluidic devices are hampered by poor capture efficiency and slow assay times.

In contrast, in the present invention, centrifugal force is also used to push and guide target particles to and against the capture surface, which increases target particle/capture site interaction thereby increasing surface capture efficiency and permitting faster fluid flow which leads to more rapid assays. In devices of the present invention, the capture surface is oriented so that it is not parallel to the plane of rotation of the platform and is positionally fixed in the device during operation of the device. Both the non-parallel orientation and positional fixing of the capture surface lead to improved capture efficiency. Thus, the direction at which the capture surface is oriented forms a non-zero angle with the plane of rotation, i.e. it is out of the plane of rotation of the platform, and therefore also forms a non-zero angle with the direction of the centrifugal force in the device. This facilitates increased interaction between the capture surface and the target particles moving in the fluid flow. Since the capture surface is also positionally fixed it is rigid and does not move around in the device thereby maintaining its non-parallel orientation. Further, the non-parallel orientation of the capture surface with respect to the plane of rotation leads to decoupling of the capture efficiency from fluid flow rate and rotational rate. Such independence of capture efficiency permits the use of faster fluid flow rates which speeds up assay time, and minimizes the need to control the rotational rate of the platform thereby simplifying operation. These are considerable advantages over existing devices.

Preferably, the angle formed between the capture surface and the plane of rotation (or the direction of centrifugal force) is in a range of from 30° to 240°, more preferably from 60° to 210°. Yet more preferably, the angle is about 90°. When the angle is 90°, the capture surface is oriented orthogonally to the plane of rotation and therefore orthogonally to the direction of centrifugal force. When the capture surface is oriented orthogonally to the plane of rotation, the capture surface is parallel to the axis of rotation of the platform. To further enhance capture efficiency, the capture surface is preferably oriented parallel to the circumferential direction of the rotating platform.

Target particles are entities on which a detection assay is desired to be performed. Such target particles may include biological or non-biological entities. Biological targets are preferred. Target particles may comprise viral particles, cells (e.g. bacterial, fungal or eukaryotic cells) or microparticles (e.g. microbeads, magnetic microparticles). Microparticles may be vehicles for carrying molecules of interest to which the assay is directed, for example, biological molecules such as proteins, carbohydrates, nucleic acids and the like. Target particles are preferably pathogens, for example viruses or cellular pathogens (e.g. bacteria or fungi), especially cellular pathogens.

The capture surface may be unfunctionalized or may be functionalized with capture moieties that bind to the target particles. If an unfunctionalized capture surface is used, the surface will have structures to participate in target particle capture. If a functionalized capture surface is used, the capture surface may be unstructured or structured. In the case of a functionalized capture surface, the type of capture moiety is selected based on the nature of the target particle. The target particle must be able to interact physically, chemically or biologically with the capture moiety. Some examples of capture moieties include small molecular entities that react with specific chemical functional groups on the target particle, antibodies, biophages and aptamers. For small molecular entities, functional group pairs that interact chemically are generally known, for example catalytic reaction of COOH and $NH_2$ or COOH and OH, where the capture moiety is selected to have one group of the pair to complement the other group of the pair on the target particle. Immuno-capture-based assays are of particular interest due to their high sensitivity and specificity. In immuno-capture-based assays the capture moiety may be, for example, a biomolecule (e.g. antibody, aptamer), a biophage, a metal or a mixture thereof. Immuno-capture-based assays are particularly useful for target particles that comprise a biological component.

The capture surface may be unstructured or structured. In the case of a structured capture surface, the surface comprises features that can capture target particles based on physical properties of the target particles, for example size, shape, mass, magnetic properties or combination thereof. Structural features include any micro- and/or nano-structured features, for example holes, posts, blazed gratings, etc. The capture surface may comprise a combination of structures for physical capture of target particles and functionalization with a capture moiety to increase specificity and efficiency of capture. In addition to facilitating physical capture of the target particles, structural features on the capture surface can increase surface area of the capture surface to increase density of capture moieties coated thereon.

The capture surface is positionally fixed in the centrifugal microfluidic device. The capture surface is preferably one or more immovable walls of a chamber or channel in the device. When the platform is rotated to generate centrifugal force, the one or more immovable walls do not move, maintaining the same orientation in respect of the rotational plane. Preferably, the capture surface is part of a capture chip comprising one or more inlets, outlets, channels and/or chambers. Flowing fluid in the device would enter the chip through the inlet, flow through the channels and/or chambers and then flow out of the chip through the outlet. One or more of the interior walls of the channels and/or chambers in the chip would be the capture surface to capture target particles flowing along with the fluid in the chip.

Microfluidic devices may comprise one or more capture surfaces designed in accordance with the present invention. Further, more than one microfluidic device may be multiplexed to form a hybrid or more complex interconnected system capable of performing multiple tasks. One or more of the devices in the system may comprise capture surfaces designed in accordance with the present invention, providing a great deal of flexibility in performing biological assays of various sorts.

Microfluidic devices generally comprise a microfluidic circuit having at least one micro-scale channel in fluid communication with at least one microfluidic chamber. Channels include, for example, sample loading channels, cell loading channels, medium perfusion channels, mixing channels, particle separation or fractionation channels, gradient generating channels and high resistance perfusion conduits, which may have different channel dimensions dictated by the specific application. Microfluidic chambers include, for example, cell culture chambers, capture chambers, biomolecular interaction chambers or mixing chambers. Other microfluidic structures may also be present, for example valves and pumps for controlling fluid flow, conduits, inlets, outlets, and the like. Channels are preferably no larger than 1 mm, at least in one direction, and the total length of the device is preferably on the order of a few centimeters to tens of centimeters. The depth of chambers, including the reservoir and siphoned chamber, may be larger than the depth of the channels in order to accommodate larger volumes of fluid, and may exceed 1 mm in size. Microfluidic devices can be readily fabricated by any of the actual microfabrication techniques known in the art, for example, machining, hot embossing, 3D printing, etc.

The device and method of the present invention is useful in many diagnostic, screening, environmental assessment and quality control applications, especially those in which there is a need for rapid and low-cost detection/identification assays. Some examples of applications include food safety, clinical diagnostics, environmental sample screening and biosecurity, where identification of bacteria and other contaminants from water samples are desired.

The present invention has several distinct advantages over the prior art. The capture efficiency is decoupled from the flow rate of the fluid near the capture surface, which his in contrast to all other known devices and methods where capture efficiency is still dependent on the fluid flow rate. In the present invention, the centrifugal force pushing target particles against the capture surface is scaled to the velocity of the flow, increasing at higher flow rates and keeping the capture efficiency flow-independent with a capture location determined by the microfluidic configuration and the target particle parameters (density, size, etc.). Moreover, this centrifugal force has a very long range of action compared to dielectrophoretic or even magnetic forces, acting identically upon all species approaching the capture surface. Consequently, a given device is characterized by a specific value of capture length and the same capture efficiency will be obtained regardless the speed of the fluid flow. Thus, the device can be easily adapted to fit regular centrifuge machines since rotation protocols and precise control of the rotation speed are not necessary. High-throughput and efficient capture of target particles is the result.

Devices of the present invention may be used in a clinical setting for rapid diagnosis of infections (in humans and carriers, such as insects) and various other diseases. Other applications include detection of, and characterization (relative to drug resistance, for example) of pathogens in various media (food, water, air) or substances (medications, devices, equipment), especially for detection of infectious agents in hospital or community settings.

The present invention is particularly appropriate for the detection of rare biomarkers or pathogens in a complex sample that is constituted of various particles (size, composition, density). The centrifugal assisted capture allows for rapid separation of the biomarker or pathogen of interest from the other constituents. One example would be for the detection of cancerous cell in a blood stream, where rare circulating tumour cells (CTCs) are present in mixture with red and white blood cells. The present invention also allows for rapid separation of the red blood cell and with the addition of surface functionalization can isolate/capture the CTCs from the white blood cells. When detached from a primary tumour and circulating in the bloodstream, CTCs may constitute seeds for subsequent growth of additional tumours (metastasis) in different tissues. As a "cancer blood test," this would be extremely useful to determine cancer stage, spread and response to treatment, thereby improving the efficiency of treatment planning.

The advantage of detecting agents that are small in number compared to components in the sample applies to most applications, including the detection of pathogens (bacteria) from a swab sample or a physiological sample. Additionally, the device and method can effectively be used for capture of bacteria or viruses from food and water samples pending sample preparations that can reduce the volume.

The present invention can be used for any kind of application in which enhanced dynamic capture is needed. Since this invention is amenable to applications in automated analysis, it may find additional, cost-effective applications in food safety, bioprocess control, defense, and veterinary medicine, and other areas.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
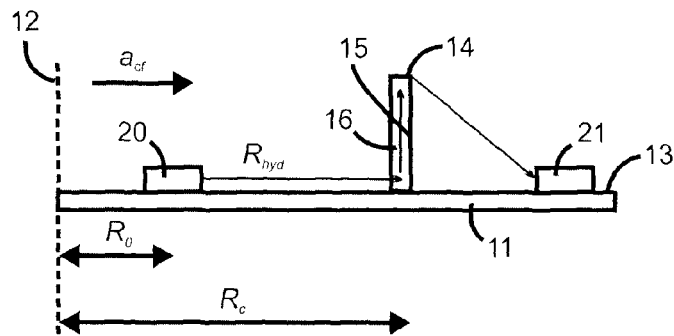
FIG. 1 depicts a schematic diagram of a centrifugal microfluidic device for centrifugally enhanced capture of target particles in accordance with the present invention.
Figure 2:
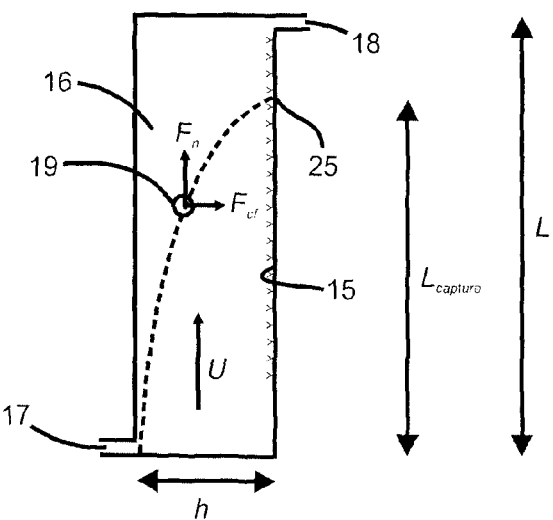
FIG. 2 depicts a vertical cross-sectional view of a capture chip in accordance with the present invention illustrating centrifugally enhanced target particle capture.

Referring to FIG. 1 and FIG. 2, a centrifugal microfluidic device for centrifugally enhanced capture of a pathogen comprises holding blade 11 that rotates around rotation axis 12. Top surface 13 of the holding blade is perpendicular to the rotation axis and therefore parallel to the rotation plane and parallel to direction of centrifugal acceleration $a_{cf}$. Mounted rigidly on the top surface of the holding blade are capture chip 14, sample reservoir 20 and waste reservoir 21. Capture chip 14 comprises capture surface 15 located in capture chamber 16. Under the influence of centrifugal force generated by rotation of the blade, a biological fluid containing the pathogen flows from sample reservoir 20 via a channel to capture chip 14, enters capture chamber 16 through inlet 17, flows through capture chamber 16 where the fluid encounters capture surface 15, and then flows out of capture chamber 16 through outlet 18 to be carried by a channel into waste reservoir 21. Because capture chip 14 is oriented perpendicularly to holding blade 11, capture surface 15, which is the bottom wall of the capture chip, is oriented orthogonally to the plane of rotation. When the biological fluid flows into the capture chamber it is forced to flow up the chip in a direction orthogonal to the plane of rotation. However, since centrifugal acceleration $a_{cf}$ is still parallel to the plane of rotation, pathogen particle 19 in capture chamber 16 experiences centrifugal force $F_{cf}$ parallel to the plane of rotation that pushes the pathogen particle toward capture surface 15, even though the fluid is flowing with velocity U and exerting a force $F_{\eta}$ on the pathogen particle in a direction perpendicular to the plane of rotation. As a consequence of the two opposed forces $F_{cf}$ and $F_{\eta}$, pathogen particle 19 follows a curved path before encountering capture surface 15.

$F_{cf}$ is a long range force field that acts identically on all objects entering the capture chip and will force the objects in the flow (e.g. pathogen particles, cells, debris, etc.) to cross fluid streamlines and curve their trajectories towards the capture surface. The centrifugal force $F_{cf}$ and fluid flow rate Q (the scalar component of fluid flow velocity U) are responsible for distance $L_{capture}$ traveled by pathogen particles from inlet 17 to capture point 25 on capture surface 15. These two important quantities (centrifugal force $F_{cf}$ and flow rate Q) can easily be tuned by the positions of sample reservoir 20 and capture chip 14 on holding blade 11 ($R_0$ and $R_c$, respectively) and the hydrodynamic resistance $R_{hyd}$ of the microfluidic circuit between the sample reservoir and the capture chip. Capture length $L_{capture}$ is given by the analytical expression:

$$L_{capture} = \frac{9\eta h}{4r_B^2 S_{chip}} \cdot \frac{R_c^2 - R_0^2}{R_c R_{hyd}} \cdot \frac{\rho}{\rho_b - \rho} \qquad \text{Eq. (1)}$$

whereas the flow rate Q is $$Q = \frac{1}{2}\rho\omega^2 \frac{R_c^2 - R_0^2}{R_{hyd}} \qquad \text{Eq. (2)}$$

In the two equations above $\eta$ is the dynamic viscosity of the fluid, h the thickness of the capture chip, $r_B$ and $\rho_b$ the radius and density of the pathogen particle respectively, $\rho$ the density of the fluid, $S_{chip}$ the cross-sectional area of the capture chip and $\omega$ the angular velocity of the microfluidic device. The condition for a 100% probability of capture is that $L_{capture} \leq L$, where L is the length of the capture chip in the direction of the fluid flow.

It can be seen from Eq. (1) that $L_{capture}$ is independent of $\omega$ whereas Q is not. This means that the $L_{capture}$ depends only on the device's geometrical setup (i.e. position of reservoirs, position of the capture chip, geometry and hydrodynamic resistance of the microfluidic circuits, etc.) and it is the same regardless of rotational speed. In contrast, the fluid flow rate Q, as shown in Eq. (2), can be tuned by adjusting the rotational speed. Consequently, the capture efficiency is decoupled from the rate of fluid flow, and for a specific geometry of the device, there is the same capture probability regardless of the rotational speed and the fluid flow rate of the biological fluid above the capture surface.

Figure 3:
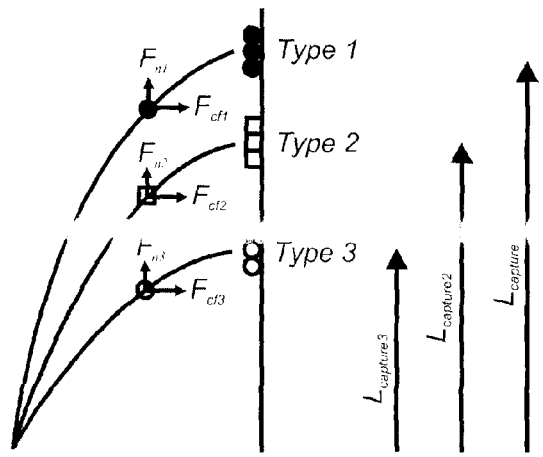
FIG. 3 depicts a schematic diagram of spatially-tuned capture of different types of target particles (Type 1, Type 2 and Type 3) on a surface, where $L_{capture1}$, $L_{capture2}$ and $L_{capture3}$ are capture lengths of each type of particle on the surface, $F_{cf1}$, $F_{cf2}$ and $F_{cf3}$ are the centrifugal forces acting on each type of particle and $F_{\eta 1}$, $F_{\eta 2}$ and $F_{\eta 3}$ are the forces due to fluid flow acting on each type of particle.

Further, it is evident from Eq. 1 that $L_{capture}$ is a function of the radius and density of the particle. Thus, in complex sample with multiple species, particles, debris of different sizes and densities, the capture of these different objects will occur at different points along the capture surface, providing a spatially distributed or tuned immobilization and separation (FIG. 3) providing the ability to separate along the flow trajectory the capture position of known target particles in the fluid. This is especially advantageous in applications such as the capture of target particles (e.g. bacteria or other cells) from complex food/water samples or the simultaneous detection of multiple pathogens.

Figure 4A:
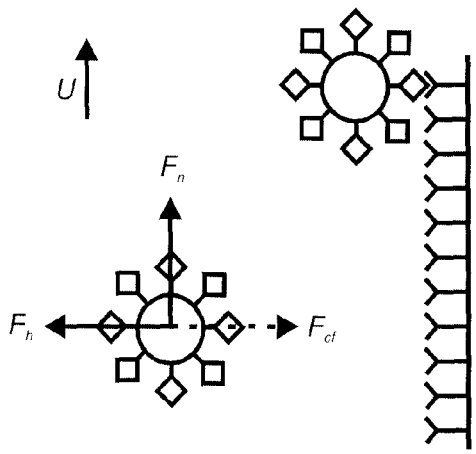
FIG. 4 depicts schematic drawings of capture surfaces for target particles in biological fluid flows over: (A) an antibody functionalized unstructured surface; (B) a micro-structured surface; and (C) an antibody functionalized micro/nano-structured surface.
Figure 4B:
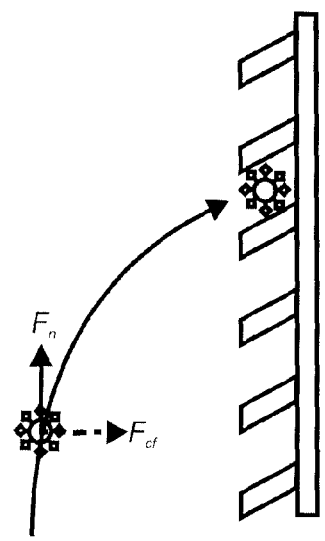
Figure 4C:
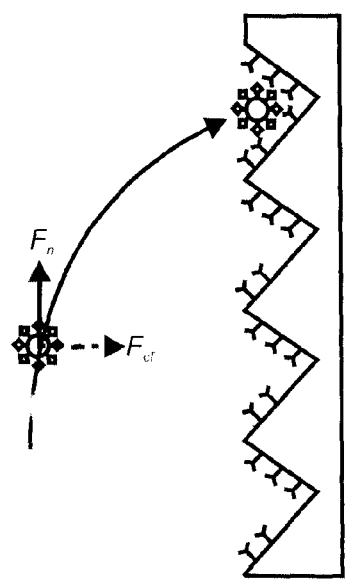

Referring to FIG. 4, the capture surface in a device of the present invention may be unfunctionalized (FIG. 4B) or functionalized with antibodies (FIG. 4A and FIG. 4C) that bind to the pathogen particles. Further, the capture surface may be unstructured (FIG. 4A) or structured with microscale features (FIG. 4B and FIG. 4C). FIG. 4A depicts an unstructured capture surface functionalized with antibodies that interact with antigens on the surface of the pathogen particle. The pathogen particle experiences centrifugal force $F_{cf}$ pushing the pathogen particle toward the capture surface, even though the fluid is flowing with velocity U and exerting a force $F_\eta$ on the pathogen particle in a direction perpendicular to the centrifugal force. Further, the "wall effect" exerts a force $F_h$ in an opposite direction as the centrifugal force pushing the pathogen particle away from the capture surface. Provided $F_{cf}$ is greater than $F_h$, the pathogen particle will eventually encounter the functionalized capture surface and be captured. In FIG. 4B, the unfunctionalized capture surface has micro-scale grooves angled against the fluid flow so that pathogen particles can be captured physically in the grooves. In FIG. 4C, the capture surface is both functionalized with antibodies and has a micro-scale grating. The grating captures pathogen particles physically while the antibodies bind to antigens on the surface of the pathogen particle thereby increasing capture efficiency.

References: The contents of the entirety of each of which are incorporated by this reference.

Amagliani G, Brandi G, et al. (2004) Direct detection of *Listeria monocytogenes* from milk by magnetic based DNA isolation and PCR. *Food Microbiology.* 21(5), 597-603.

Andersson P, Thorsen G, Kylberg G. (2003) Functional Unit Enabling Controlled Flow in a Microfluidic Device. United States Patent Publication US 2003-0053934 published Mar. 20, 2003.

Carvalho B L, Sheppard Jr. N F, Feakes C, Kellogg G J. (2004) Microfluidics Devices and Methods for Performing Cell Based Assays. U.S. Pat. No. 6,818,435 issued Nov. 16, 2004.

Choi J-W, Pu A, et al. (2006) Bacteria Detection in a Microfluidic Channel Utilizing Electromagnetic Cellular Polarization and Optical Scattering. 2006 *Digest of the LEOS Summer Topical Meetings.* 2, 17-18.

Choi W. (2002) Rapid enumeration of *Listeria monocytogenes* in milk using competitive PCR. *International journal of food microbiology.* 84, 79-85.

Desmond S M, Shigeura J. (2006) Micro-channel Design Features that Facilitate Centripetal Fluid Transfer. U.S. Pat. No. 7,041,258 issued May 9, 2006.

Dwivedi H P, Jaykus L A. (2011) Detection of pathogens in foods: The current state-of-the-art and future directions. *Critical Reviews in Microbiology.* 37(1), 40-63.

Firstenberg-Eden R, Shelef L A. (2000) A new rapid automated method for the detection of *Listeria* from environmental swabs and sponges. *International journal of food microbiology.* 56(2-3), 231-237.

Garcia Da Fonseca J, Esteves Reis N A, Burger R. (2010) Analytical Rotors and Methods for Analysis of Biological Fluids. International Patent Publication WO 2010-077159 published Jul. 8, 2010.

Garcia-Cordero J L, Dimov I K, O'Grady J, Ducrée J, Barry T, Ricco A J. (2009) Monolithic Centrifugal Microfluidic Platform for Bacteria Capture and Concentration, Lysis, Nucleic-Acid Amplification, and Real-Time Detection. *MEMS 2009—22nd IEEE International Conference on Micro Electro Mechanical Systems.* pp. 356-359.

Gui J Y, Tian W-C, Phukan A, Thutupalli S, Samper V. (2007) Rotation-based Microsampler, System and Method of Using the Same. United States Patent Publication US 2007-0224591 published Sep. 27, 2007.

Hurt S N, Gordon J F, McIntyre K R. (2006) Method and Apparatus for Blood Typing with Optical Bio-discs. U.S. Pat. No. 7,026,131 issued Apr. 11, 2006.

Inganas M, Soderman T, Hogstrand E. (2008) Liquid Detection and Confidence Determination. United States Patent Publication US 2008-0138247 published Jun. 12, 2008.

Ingianni A, Floris M, et al. (2001) Rapid detection of *Listeria monocytogenes* in foods, by a combination of PCR and DNA probe. *Molecular and cellular probes.* 15(5), 275-280.

Jung E K Y, Leuthardt E C, Levien R A, Lord R W, Malamud M A, Rinaldo J D, Wood L L. (2008) Systems for Pathogen Detection. United States Patent Publication US 2008-0241000 published Oct. 2, 2008.

Kaittanis C, Naser S A, Perez J M. (2007) One-Step, Nanoparticle-Mediated Bacterial Detection with Magnetic Relaxation. *Nano Letters.* 7(2), 380-383.

Kido H, Norton J R, Coombs J H. (2005) Fluidic Circuits for Sample Preparation Including Bio-discs and Methods Relating Thereto. United States Patent Publication US 2005-0047968 published Mar. 3, 2005.

Kim S-h. (2010) Optical Detection Apparatus, Optical Detection Method, and Microfluidic System Including the Optical Detection Apparatus. U.S. Pat. No. 7,692,794 issued Apr. 6, 2010.

Koubová V, Brynda E, et al. (2001) Detection of foodborne pathogens using surface plasmon resonance biosensors. *Sensors and Actuators B: Chemical.* 74(1-3), 100-105.

Lee B-s, Cho Y-k, Lee J-g, Park J-m. (2010) Centrifugal Force-Based Microfluidic Device for Protein Detection and Microfluidic System Including the Same. U.S. Pat. No. 7,776,267 issued Aug. 17, 2010.

Lee B-s, Cho Y-k, Lee J-g, Park J-m. (2011) Centrifugal Force-Based Microfluidic Device for Protein Detection and Microfluidic System Including the Same. United States Patent Publication US 2011-020194 published Jan. 27, 2011.

Li H, Bashir R. (2002) Dielectrophoretic separation and manipulation of live and heat-treated cells of *Listeria* on microfabricated devices with interdigitated electrodes. *Sensors and Actuators B: Chemical.* 86(2-3), 215-221.

Li P C H, Peng X Y, Yu H Z, Parameswaren M, Chen H, Chou W L. (2010) Microfluidic Microarray Assemblies and Methods of Manufacturing and Using. United States Patent Publication US 2010-0041562 published Feb. 18, 2010.

Madonna A J, Basile F, et al. (2001) Detection of bacteria from biological mixtures using immunomagnetic separation combined with matrix-assisted laser desorption/ionization time-of-flight mass spectrometry. *Rapid communications in mass spectrometry: RCM.* 15(13), 1068-1074.

Niwa D. (2011) Separation Purification Method and Microfluidic Circuit. United States Patent Publication US 2011-0003285 published Jan. 6, 2011.

Nolte D D. (2009) Review of centrifugal microfluidic and bio-optical disks. *Review of Scientific Instruments.* 80, 101101 (22 pages).

Ostlin H, Eriksson L, Ljungstrom M, Agren T. (2007) Detector Arrangement Based on Surfaces Plasmon resonance. U.S. Pat. No. 7,295,320 issued Nov. 13, 2007.

Sewell A M, Warburton D W, et al. (2003) The development of an efficient and rapid enzyme linked fluorescent assay method for the detection of *Listeria* spp. from foods. *International journal of food microbiology.* 81(2), 123-129.

Su X-L, Li Y. (2004) Quantum dot biolabeling coupled with immunomagnetic separation for detection of *Escherichia coli* 0157:H7. *Analytical chemistry.* 76(16), 4806-4810.

Tooke N E, Andersson P X. (2008) Integrated Microfluidic Disc. U.S. Pat. No. 7,332,126 issued Feb. 19, 2008.

Vaughan R, O'Sullivan C K, Guilbault G G. (2001) Development of a quartz crystal microbalance (QCM) immunosensor for the detection of *Listeria monocytogenes*. *Enzyme and microbial technology*. 29(10), 635-638.

Wawerla M, Stolle A, et al. (1999) Impedance Microbiology: Applications in Food Hygiene. *Journal of Food Protection*. 62, 1488-1496.

Yang L, Banada P P, et al. (2006) A multifunctional microfluidic system for dielectrophoretic concentration coupled with immuno-capture of low numbers of *Listeria monocytogenes*. Lab on a chip. 6(7), 896-905.

Zeng L, Balanchadar S, Fischer P. (2005) Wall-induced forces on a rigid sphere at finite Reynolds number. *Journal of Fluid Mechanics*. 536, 1-25.

Zourob M, Elwary S, et al. (2008) *Principles of Bacterial Detection—Biosensors, Recognition Receptors and Mycrosystems*. New York, Springer Science+Business Media, LLC.

Zucchelli P, Van de Vyver B. (2006) Devices and Methods for Programmable Microscale Manipulation of Fluids. U.S. Pat. No. 7,152,616 issued Dec. 26, 2006.

Other advantages that are inherent to the structure are obvious to one skilled in the art. The embodiments are described herein illustratively and are not meant to limit the scope of the invention as claimed. Variations of the foregoing embodiments within the scope of the claimed and generally disclosed invention will be evident to a person of ordinary skill and are intended by the inventor to be encompassed by the following claims.

The invention claimed is:

1. A centrifugal microfluidic device for conducting capture assays, the device comprising:
   a microfluidic platform having an axis of rotation about which it rotates, the axis being perpendicular to a plane of rotation;
   a sample reservoir and a capture chip defined on the platform;
   a capture chamber on the capture chip for receiving fluid from the sample reservoir via an inlet; and
   at least one capture surface for immobilizing a target particle of interest in the device, the at least one capture surface being at least one internal wall of the capture chamber,
   wherein:
   the at least one capture surface is positionally fixed in the device during operation of the device in an orientation that is not parallel to the plane of rotation of the device;
   the at least one capture surface and inlet are arranged so fluid entering into the capture chamber is forced to flow in a direction orthogonal to the plane of rotation; and
   centrifugal force arising from rotation of the device forces the target particles against the at least one capture surface.

2. The device according to claim 1, wherein the at least one capture surface and the plane of rotation form an angle in a range of from 30° to 240°.

3. The device according to claim 1, wherein the at least one capture surface and the plane of rotation form an angle in a range of from 60° to 210°.

4. The device according to claim 1, wherein the at least one capture surface is orthogonal to the plane of rotation.

5. The device according to claim 1, wherein the at least one capture surface is oriented parallel to a circumferential direction of the rotating platform.

6. The device according to claim 1, wherein the at least one capture surface is orthogonal to the plane of rotation and has a length (L) that is equal to or longer than a capture length ($L_{capture}$) given by:

$$L_{capture} = \frac{9\eta h}{4r_B^2 S_{chip}} \cdot \frac{R_c^2 - R_0^2}{R_c R_{hyd}} \cdot \frac{\rho}{\rho_b - \rho} \qquad \text{Eq. (1)}$$

wherein $\eta$ is dynamic viscosity of the fluid flowing in the capture chamber, h is thickness of the capture chip, $r_B$ is radius of the target particle, $\rho_b$ is the density of the target particle, $\rho$ is the density of the fluid, $S_{chip}$ is the cross-sectional area of the capture chip, $R_0$ is a distance from center of the sample reservoir to the axis of rotation, $R_c$ is a distance from the at least one capture surface to the axis of rotation and $R_{hyd}$ is hydrodynamic resistance in the microfluidic device between the sample reservoir and the capture chip.

7. The device according to claim 1, wherein the target particle comprises a pathogen.

8. The device according to claim 1, wherein the at least one capture surface is functionalized with capture moieties that interact with the target particle.

9. The device according to claim 8, wherein the capture moieties are biomolecules, biophages, antibodies, aptamers or mixtures thereof.

10. The device according to claim 1, wherein the at least one capture surface is structured with micro- and/or nano-structured features.

11. A method of capturing a target particle of interest for an assay in a centrifugal microfluidic device, the method comprising:
   introducing a fluid containing the target particle into a sample reservoir of a rotatable microfluidic platform of the microfluidic device;
   rotating the microfluidic platform in a plane of rotation to generate centrifugal force in the device; and,
   using the centrifugal force to direct flow of the fluid from the sample reservoir to a capture chamber via an inlet, the capture chamber having at least one capture surface being at least one internal wall of the capture chamber,
   where the at least one capture surface and inlet are arranged so fluid entering into the capture chamber is forced to flow in a direction orthogonal to the plane of rotation such that the fluid strikes the at least one capture surface and thereby pushes the target particle against the at least one capture surface to increase a probability of the target particle interacting with the at least one capture surface, and
   capture efficiency of the at least one capture surface for the target particle is independent of rate of flow of the fluid and independent of rate of rotation of the microfluidic platform.

12. The method according to claim 11, wherein the at least one capture surface is oriented out of the plane of rotation thereby forming a non-zero angle between the at least one capture surface and direction of the centrifugal force.

13. The method according to claim 11, wherein the at least one capture surface is oriented orthogonally to the plane of rotation thereby forming a perpendicular angle between the at least one capture surface and direction of the centrifugal force.

14. The method according to claim 11, wherein the at least one capture surface is oriented parallel to a circumferential direction of the rotating platform.

15. The method according to claim 11, wherein the microfluidic platform comprises a capture chip comprising the at least one capture surface, wherein the at least one capture surface is orthogonal to the plane of rotation and has a length (L) that is equal to or longer than a capture length ($L_{capture}$) given by:

$$L_{capture} = \frac{9\eta h}{4r_B^2 S_{chip}} \cdot \frac{R_c^2 - R_0^2}{R_c R_{hyd}} \cdot \frac{\rho}{\rho_b - \rho} \qquad \text{Eq. (1)}$$

wherein $\eta$ is dynamic viscosity of the fluid flowing in the capture chamber, h is thickness of the capture chip, $r_B$ is radius of the target particle, $\rho_b$ is the density of the target particle, $\rho$ is the density of the fluid, $S_{chip}$ is the cross-sectional area of the capture chip, $R_0$ is a distance from center of the sample reservoir to the axis of rotation, $R_c$ is a distance from the at least one capture surface to the axis of rotation and $R_{hyd}$ is hydrodynamic resistance in the microfluidic device between the sample reservoir and the capture chip.

16. The method according to claim 11, wherein the target particle comprises a pathogen.

17. The method according to claim 11, wherein the at least one capture surface is functionalized with capture moieties that interact with the target particle.

18. The method according to claim 17, wherein the capture moieties are biomolecules, biophages, antibodies, aptamers or mixtures thereof.

19. The method according to claim 11, wherein the at least one capture surface is structured with micro- and/or nano-structured features.

* * * * *